United States Patent [19]

Durual et al.

[11] Patent Number: 5,382,723
[45] Date of Patent: Jan. 17, 1995

[54] SYNTHESIS OF HYDROGEN PERFLUOROALKANES

[75] Inventors: Pierre Durual; André Lantz, both of Vernaison, France

[73] Assignee: Elf Atochem S.A., France

[21] Appl. No.: 186,493

[22] Filed: Jan. 26, 1994

Related U.S. Application Data

[63] Continuation of Ser. No. 834,097, Feb. 12, 1992, abandoned.

[30] Foreign Application Priority Data

Feb. 12, 1991 [FR] France ................. 91 01617

[51] Int. Cl.$^6$ ............................................. C07C 19/08
[52] U.S. Cl. .................................................. 570/176
[58] Field of Search ........................................ 570/176

[56] References Cited

U.S. PATENT DOCUMENTS 4,929,318  5/1990  Furutaka et al. .

FOREIGN PATENT DOCUMENTS 308923   3/1989  European Pat. Off. ............ 570/176
1600040  1/1968  France .............................. 570/176
2116524  7/1972  France .
1364495  8/1974  United Kingdom .

OTHER PUBLICATIONS

Journal of the Chemical Society, 1951, Letchworth GB, pp. 60–64.
J. Banus, et al.: "The Heterolytic Fission of the Carbon–Iodine Bond in Trifluoroidomethane".

Primary Examiner—Alan Siegel
Attorney, Agent, or Firm—Morgan & Finnegan

[57] ABSTRACT

The invention relates to the synthesis of hydrogenperfluoroalkanes $R_FH$, $R_F$ denoting a perfluoroalkyl radical containing 2 to 20 carbon atoms, by reaction of the corresponding perfluoroalkyl iodide $R_FI$ with an alkali metal hydroxide.

The use of methanol as solvent allows the formation of tars to be avoided, an almost total conversion of $R_FI$ and an $R_FH$ of excellent purity to be obtained, and the alkali metal iodide by-product to be recovered easily.

14 Claims, No Drawings

SYNTHESIS OF HYDROGEN PERFLUOROALKANES

This is a continuation of co-pending application Ser. No. 07/834,097, filed on Feb. 12, 1992 now abandoned.

FIELD OF THE INVENTION

The present invention relates to the field of fluorinated aliphatic hydrocarbons and more particularly to the preparation of hydrogenperfluoroalkanes $R_FH$, $R_F$ denoting a linear or branched perfluoroalkyl radical which can contain 2 to 20 carbon atoms, preferably 2 to 10.

BACKGROUND OF THE INVENTION

The hydrogenperfluoroalkanes are known compounds which can be used, for example, as inert fluids in the electronic field, as heat transfer fluids or as intermediate products for the synthesis of other fluorinated compounds, for example for the preparation of perfluoroalkyl bromides $R_FBr$, of which some (especially $C_8F_{17}Br$) have found an application in medicine as radiopaques (X-ray contrast agents) or as oxygen carriers in blood substitutes.

Among the numerous methods known to prepare hydrogenperfluoroalkanes, the most attractive, because they start from perfluoroalkyl iodides $R_FI$ which are industrial products, consist in reacting a compound $R_FI$ with alcoholic potash at a temperature of 100° to 130° C. (see J. Banus et al, J. Chem. Soc. 1951, 60 and particularly R. N. Haszeldine, J. Chem. Soc. 1953, 3761-8) or with hydrogen under pressure in the presence of Raney nickel (R. N. Haszeldine, ibid. and French Patent 2,116,524).

Although it appears to give the best yields (>80%), this last method has the disadvantage, on the one hand, of being carried out in an autoclave under a pressure of several tens of bars of hydrogen and, on the other hand, of not leading to a total selectivity because doubling products $R_F$—$R_F$ are formed which contaminate the hydrogenperfluoroalkanes obtained.

The first method (treatment of the $R_FI$ by alcoholic potash) does not have these disadvantages, but unfortunately leads to a yield of compound $R_FH$ (27 to 51%) which is lower as the number of carbon atoms of the radical $R_F$ is increased (51% for $C_3F_7H$ and 27% for $C_8F_{17}H$). In addition, the formation of tars is seen which prevent the filtration of the reaction mixture and render impossible the recovery of the potassium iodide by-product. It is the same when ethanol is replaced by isopropanol, used in U.S. Pat. No. 4,618,731 in relation to the purification of 2-perfluoroalkylethanols containing the compounds $R_FCH_2CH_2I$ and $R_FI$ as impurities.

DESCRIPTION OF THE INVENTION

It has now been found in a quite unexpected manner that methanol does not lead to the formation of tars and allows not only an almost complete conversion of the starting $R_FI$ to be obtained, but also an $R_FH$ of excellent purity. The use of methanol in addition allows the major part of the alkali metal iodide by-product to be recovered.

The invention thus relates to a process for the preparation of a hydrogenperfluoroalkane $R_FH$ by reaction of the corresponding perfluoroalkyl iodide $R_FI$ with an alkali metal hydroxide, characterized in that it is carried out in methanol.

As alkali metal hydroxide, it is preferred to use potassium hydroxide because the potassium iodide by-product, which can be easily recovered with an excellent purity owing to the use of methanol, is a product in demand on the market. However, it will not be outside the scope of the present invention to use the hydroxide of another alkali metal such as, for example, sodium hydroxide. The quantity of alkali metal hydroxide to be used per mole of $R_FI$ can range from 1 to 5 mol; it is preferably between 1.5 and 3 mol.

The quantity of methanol to be used can vary within wide limits. However, it must be sufficient for a partial solubilization of the reagents such as to ensure sufficient contact to carry out the reaction. A quantity of methanol ranging from 0.25 to 3 liters, preferably 0.5 to 1.5 liters per kilogram of $R_FI$ employed is generally highly suitable.

The process according to the invention can be carried out by employing all of the reagents ($R_FI$, alkali metal hydroxide, methanol) from the start. However, to avoid possible violent reaction due to the exothermic nature of the reaction, it is preferable to add in a progressive fashion (for example in 1 to 20 hours and preferably in 2 to 8 hours) either the $R_FI$ to the methanolic alkali hydroxide solution, or this last solution to a methanolic solution of $R_FI$.

The reaction can be carried out at a temperature ranging from 10° to 66° C., the optimum temperature depending on the $R_FH$ under consideration.

The hydrogenperfluoroalkane formed can be recovered by distillation of the reaction mixture. This distillation gives either the $R_FH$ itself (in the case of $C_2$ to $C_4$ compounds), or an $R_FH$/methanol azeotrope (in the case of heavy compounds such as $C_6F_{13}H$ or $C_6F_{17}H$); washing the azeotrope with water allows the $R_FH$ to be isolated in an extremely pure form.

It can also be advantageous to distil the $R_FH$ or the $R_FH$/methanol azeotrope continuously, in particular in the case where the reaction is carried out in a progressive manner by adding the $R_FI$ to the methanolic alkaline metal hydroxide solution or by adding the methanolic alkali metal hydroxide solution to a methanolic solution of $R_FI$.

EXAMPLES

The following examples illustrate the invention without limiting it. The percentages are expressed in terms of weight.

EXAMPLE 1

1 liter of methanol and 198 g of 85% potash (3 mol of KOH) are introduced into a 2-liter reactor fitted with a stirrer, a thermometer, a dropping funnel and on top of which is a distillation column having a glass packing followed by a condenser, then 1092 g (2 mol) of perfluorooctyl iodide are introduced with stirring in the course of 2 hours. The reaction is exothermic.

By heating, a $C_8F_{17}H$/methanol azeotrope (59:41) is distilled at 62°-63° C. and collected in 500 g of water for 5 hours. By decantation, a lower phase (825 g) composed of $C_8F_{17}H$ of 99.4% purity is separated. Yield: 97.6%.

By filtration of the bottom of the reactor, 279 g of a solid composed of potassium iodide of 97% purity is obtained (yield: 84%).

EXAMPLE 2 (COMPARATIVE)

The process is as in Example 1, but replacing the methanol by the same quantity of ethanol and using only 132 g of 85% potash (2 mol of KOH).

After 3 hours of distillation at 78° C. at the head (ethanol), it is noted that the reaction has stopped. 499 g of a mixture composed of 84.4% of $C_8F_{17}H$, 12.8% of ethanol and 1.3% of $C_8F_{17}I$ have been collected, i.e. a yield of 50%.

The reaction mixture remaining in the reactor is completely black. 132 g of 85% potash are added to it, then the distillation is resumed for 2 hours. The reaction again stops and 258 g of product containing 81% of $C_8F_{17}H$, 16.6% of ethanol and 1.6% of $C_8F_{17}I$ are collected, which raises the overall yield to 75%. The contents of the reactor are present in the form of a tarry, unfilterable black mass.

EXAMPLE 3 (COMPARATIVE)

Example 1 is reproduced, but replacing the methanol by isopropanol. By distillation up to 74° C., 102 g of a homogeneous phase containing 20.6% of $C_8F_{17}H$, 21.8% of isopropanol and 57.1% of acetone are collected.

Continuing the distillation at 74°-76° C., a product is collected which separates into two phases, the lower phase (250 g) containing 67.4% of $C_8F_{17}H$, 24.1% of isopropanol and 8.2% of acetone. The overall yield of $C_8F_{17}H$ is 22.6%.

At the end of distillation, the contents of the reactor solidify in a black mass which prevents stirring, which leads to the experiment being stopped.

EXAMPLE 4

The procedure is as in Example 1 with 400 ml of methanol, 107 g of 85% potash (1.62 mol of KOH) and 446 g (1 mol) of perfluorohexyl iodide.

After distillation at 52.5°-53° C. of the $C_6F_{13}H$/methanol azeotrope (89:11), the distillation is continued up to 60° C. at the head, then the distillate (332 g) is poured into 200 ml of water. After separation, the lower phase is washed with 200 ml of water. 289 g of $C_6F_{13}H$ of 99.7% purity are thus obtained. Yield: 90%.

EXAMPLE 5

1.5 liter of methanol and 296.5 g of 85% potash (4.5 mol of KOH) are introduced into a 4-liter reactor, equipped with a stirrer, a thermometer and a distillation column with a glass packing, and cooled to −20° C. The mixture is raised to 35° C., then 1038 g (3 mol) of perfluorobutyl iodide are introduced in the course of 4 hours while maintaining the temperature of the reaction mixture at 40°-45° C.

During the introduction of the $C_4F_9I$, the nonafluorobutane $C_4F_9H$ formed is distilled at the head (T=16° C.). This compound, which does not form an azeotrope with methanol, is collected in a flask cooled in an ice bath.

After the end of the introduction of the $C_4F_9I$, the distillation is continued up to 62° C. at the head so as to recover all of the $C_4F_9H$ formed. 647 g of $C_4F_9H$ of 99.3% purity (0.1% of perfluorooctane, 0.2% of entrained $C_4F_9I$ and 0.3% of methanol) are thus obtained. Yield: 97.3%.

EXAMPLE 6

Two 1-liter reactors are used, arranged in series and fitted with means for stirring and heating. A solution of 99 g of 85% potash (1.5 mol of KOH) in 0.5 liter of methanol is introduced into the first reactor and a solution of 20 g of 85% potash (0.3 mol of KOH) in 0.5 liter of methanol is introduced into the second reactor.

The first reactor is heated to 30° C., then 246 g (1 mol) of pentafluoroethyl iodide are introduced into it in the course of 7 hours while keeping at 30°-35° C. with stirring.

The gases pass into the second reactor which is stirred and kept at 20°-25° C., then into a water wash bottle to eliminate the entrained methanol. They are then dried on $CaCl_2$ before being collected in a trap cooled by dry ice.

The introduction of $C_2F_5I$ being complete, the contents of the first reactor are heated to reflux, and then those of the second reactor to recover all of the $C_2F_5H$ dissolved.

114 g of pentafluoroethane containing 2% of residual $C_2F_5I$ are thus obtained. Yield of $C_2F_5H$: 93.1%.

EXAMPLE 7

200 ml of methanol and 1184 g (4 mol) of perfluoroisopropyl iodide are introduced into a 2-liter reactor, fitted with a stirrer, a thermometer, a dropping funnel and on top of which is a first distillation-column part with a glass packing cooled with water, then a second identical part cooled to −25° C.

The reactor is heated to 40° C., then a solution of 420 g of 85% potash (6.4 mol of KOH) in 1.2 liters of methanol is introduced in the course of 2 and a half hours, keeping at 40°-45° C. During the introduction of this solution, the $C_3F_7H$ distils and it is collected in a trap cooled by dry ice.

After all of the solution of methanolic potash has been introduced, the contents of the reactor are heated up to 66° C. to recover all of the $C_3F_7H$ formed. 667.5 g of $C_3F_7H$ of 99.5% purity are thus collected, i.e. a yield of 97.7%.

What is claimed is:

1. Process for the preparation of a hydrogenperfluoroalkane $R_FH$, $R_F$ denoting a linear or branched perfluoroalkyl radical containing 2 to 20 carbon atoms and alkali metal iodide, consisting essentially in reacting the corresponding perfluoroalkyl iodide $R_FI$ with methanol and an alkali metal hydroxide or an aqueous solution thereof, whereby tar formation is avoided, and recovering the hydrogen perfluoroalkane formed and the alkali metal iodide by-product from the reaction mixture.

2. Process according to claim 1, wherein the alkali metal hydroxide is potassium hydroxide.

3. Process according to claim 1, wherein the quantity of alkali metal hydroxide, used per mole of $R_FI$, is between 1 and 5 mol.

4. Process according to claim 1, wherein the quantity of methanol, used per kg of $R_FI$, is between 0.25 and 3 liters.

5. Process according to claim 1, wherein the $R_FI$ is introduced into a methanolic alkali metal hydroxide solution in a progressive manner.

6. Process according to claim 1, wherein a methanolic alkali metal hydroxide solution is introduced into a methanolic solution of $R_FI$.

7. Process according to claim 1, wherein the reaction is conducted at a temperature between 10° and 66° C.

8. Process according to claim 1, wherein the reaction is carried out at a temperature sufficient to distil the $R_FH$ formed or its azeotrope with methanol.

9. Process according to claim 8, wherein potassium hydroxide is used and the potassium iodide by-product is recovered by filtration of the residual reaction mixture.

10. Process according to claim 1, wherein the synthesis is of $C_2$ to $C_{10}$ hydrogenperfluoroalkanes.

11. Process according to claim 3, wherein the quantity of alkali metal hydroxide is between 1.5 and 3 mol.

12. Process according to claim 4, wherein the quantity of methanol is between 0.5 and 1.5 liters.

13. Process according to claim 5, wherein the progressing manner is in the course of 2 to 8 hours.

14. Process according to claim 10, wherein the hydrogenperfluoroalkane is $C_8F_{17}H$.

* * * * *